(12) United States Patent
Walzman

(10) Patent No.: US 10,898,678 B2
(45) Date of Patent: Jan. 26, 2021

(54) SEGMENTED ARCH FULCRUM SUPPORT CATHETER AND METHOD OF USE

(71) Applicant: Daniel Ezra Walzman, Bergenfield, NJ (US)

(72) Inventor: Daniel Ezra Walzman, Bergenfield, NJ (US)

(73) Assignee: Daniel Ezra Walzman, Bergenfield, NJ (US)

( * ) Notice: Subject to any disclaimer, the term of this patent is extended or adjusted under 35 U.S.C. 154(b) by 189 days.

(21) Appl. No.: 15/998,041

(22) Filed: Jun. 15, 2018

(65) Prior Publication Data
US 2019/0381277 A1 Dec. 19, 2019

(51) Int. Cl.
*A61M 25/00* (2006.01)
(52) U.S. Cl.
CPC .... *A61M 25/0041* (2013.01); *A61M 25/0043* (2013.01); *A61M 2025/006* (2013.01); *A61M 2025/0059* (2013.01); *A61M 2205/0216* (2013.01); *A61M 2205/0266* (2013.01)

(58) Field of Classification Search
CPC ............ A61B 17/3423; A61B 17/3415; A61B 2017/3425; A61M 25/09041; A61M 25/0662; A61M 25/0041; A61M 25/0026; A61M 2210/127; A61F 2/954
See application file for complete search history.

(56) References Cited

U.S. PATENT DOCUMENTS

| | | | |
|---|---|---|---|
| 5,868,700 A * | 2/1999 | Voda | A61M 25/0041 604/264 |
| 6,547,760 B1 | 4/2003 | Samson et al. | |
| 6,723,116 B2 | 4/2004 | Tahiri | |
| 2005/0015007 A1* | 1/2005 | Itou | A61M 25/0041 600/433 |

* cited by examiner

*Primary Examiner* — Anh T Dang

(57) ABSTRACT

The present disclosure teaches a medical device and method of use, employing a tube which is composed of segments and bends capable being configured into unique shape that allows said device to use the lesser (inferior) curve of aortic Arch and other vessel structures as as fulcrums of support for a guide catheter, for subsequent prevention of recoil and displacement thereof, while delivering additional catheters or devices into the distal branches of the great vessels. A method for using same.

9 Claims, 2 Drawing Sheets

SEGMENTED ARCH FULCRUM SUPPORT CATHETER AND METHOD OF USE

CROSS-REFERENCE(S)

This is a continuation-in-part application claiming the benefit of priority to U.S. Non-Provisional application Ser. No.: 15/932,775 filed Apr. 23, 2018, which in turn claims priority to claiming the benefit of priority to U.S. Non-Provisional application Ser. No.: 15/250,693 filed Aug. 29, 2016, which in turn claims priority to Non-Provisional application Ser. No. 15/158,341 filed on May 18, 2016, the entire contents of which are incorporated by reference.
Date Filed Jun. 15, 2018 (15-JUN-2018)
USPS Prio. Expr. Mail No. EK 653560944 US
Practitioner Docket no.: WAL238-269677
Examiner/Art Unit n/a

FIELD OF THE INVENTION

The described invention relates generally to endovascular devices and more particularly to a segmented shaped support catheter and a method of use of said segmented shaped support catheter.

BACKGROUND OF THE INVENTION

Carotid Access Safety

Safe carotid access with a guide catheter or sheath is among the first steps employed in a carotid stent procedure. Due to the tortuous anatomy and the three-dimensional arch structures anchoring stents using existing techniques requires a steep learning curve and extensive monitoring may result in adverse radiation exposure for the patient. Besides embolism, several complications can occur during carotid access, including dissection of the carotid arteries caused by the ledge effect due to unopposed space between a larger guide catheter (7-9 F) and a smaller diagnostic catheter and guide-wire-related branch arterial perforations. The small branch perforations can be deadly, due to the rapid development of retropharyngeal bleeding and airway compromise particularly with an anti-coagulated patient. The most dreaded complication associated with the remote guide catheter access method is guide catheter prolapse, with the carotid filter getting entangled in the stent and detaching or embolizing. Additionally, cerebral embolism during carotid access is a risk during a carotid stent procedure.

Additionally, access to the carotid and vertebral arteries, as well as occasionally to other vessels, can sometimes be impossible to achieve in routine transfemoral fashion in certain anatomical situations. This is especially difficult with type III aortic arches. In many cases this can altogether prevent treatment of critical illnesses such as acute thromboembolic stroke, brain aneurysms, and other pathology.

Device Recoil Difficulties

Medical devices such as catheters are commonly used in the diagnosis and treatment of various medical conditions. Advancements in catheter designs and materials have made them particularly well-suited for intravascular procedures and intravascular therapies. Typically a catheter includes a small, elongated tube made of flexible, biocompatible materials that enable the catheter to be easily maneuvered through body passages and vascular structures. During a representative procedure, the distal end of the catheter is inserted into the body via small incisions in the groin area or upper arm and guided through blood vessels to a target site using guide wires and associated imaging techniques. The proximal end is then connected to the device for performing the desired procedures.

However, in many anatomical situations, access to some vessels can be difficult. This is especially the case when tortuosity and/or the particular anatomy creates additional bends along the desired course of the catheter. In such cases, when a wire is advanced around the band, a counterforce is created that tends to kick back the wire and catheter that the wire is being advanced through. If the catheter does not have adequate physical support to resist such recoil and displacement, it will fall out of the desired position. In some cases this could prevent appropriate access to the desired pathological region altogether. In other cases, it can create complications during a procedure when catheters and devices suddenly recoil and displacement and are dislodged from the desired location. Such movement is undesirable.

Blood Vessel Structure and Function

Blood vessels arc dynamic structures that constrict, relax, pulsate, and proliferate. Within the body, blood vessels form a closed delivery system that begins and ends at the heart. There are three major types of blood vessels: (i) arteries; (ii) capillaries and (iii) veins. As the heart contracts, it forces blood into the large arteries leaving the ventricles. Blood then moves into smaller arteries successively, until finally reaching the smallest branches, the arterioles, which feed into the capillary beds of organs and tissues. Blood drains from the capillaries into venules, the smallest veins, and then into larger veins that merge and ultimately empty into the heart.

Arteries carry blood away from the heart and "branch" as they form smaller and smaller divisions. In contrast, veins carry blood toward the heart and "merge" into larger and larger vessels approaching the heart. In the systemic circulation, arteries carry oxygenated blood and veins carry oxygen-poor blood. In the pulmonary circulation, the opposite is true. The arteries (as the vessels leading away from the heart), carry oxygen-poor blood to the lungs, and the veins carry oxygen-rich blood from the lungs to the heart.

The only blood vessels that have intimate contact with tissue cells in the human body are capillaries. In this way, capillaries help serve cellular needs. Exchanges between the blood and tissue cells occur primarily through the thin capillary walls.

The walls of most blood vessels (the exception being the smallest vessels, e.g., venules), have three layers, or tunics, that surround a central blood-containing space called the vessel lumen.

The innermost tunic (layer) is the tunica intima. The tunica intima contains the endothelium, the simple squamous epithelium that lines the lumen of all vessels. The endothelium is continuous with the endocardial lining of the heart, and its flat cells fit closely together, forming a slippery surface that minimizes friction so blood moves smoothly through the lumen. In vessels larger than 1 mm in diameter, a sub-endothelial layer, consisting of a basement membrane and loose connective tissue, supports the endothelium.

The middle tunic (layer), the tunica media, is mostly circularly arranged smooth muscle cells and sheets of elastin. The activity of the smooth muscle is regulated by sympathetic vasomotor nerve fibers of the autonomic nervous system. Depending on the body's needs at any given time, regulation causes either vasoconstriction (lumen diameter decreases) or vasodilation (lumen diameter increases). The activities of the tunica media are critical in regulating the circulatory system because small changes in vessel diameter greatly influence blood flow and blood pressure.

Generally, the tunica media is the bulkiest layer in arteries, which bear the chief responsibility for maintaining blood pressure and proper circulation.

The outer layer of a blood vessel wall, the tunica externa, is primarily composed of collagen fibers that protect the vessel, reinforce the vessel, and anchor the vessel to surrounding structures. The tunica externa contains nerve fibers, lymphatic vessels, and elastic fibers (e.g., in large veins). In large vessels, the tunica externa contains a structure known as the vasa vasorum, which literally means "vessels of vessels". The vasa vasorum nourishes external tissues of the blood vessel wall. Interior layers of blood vessels receive nutrients directly from blood in the lumen (See, e.g., The Cardiovascular System at a Glance, 4th Edition, Philip I. Aaronson, Jeremy P. T. Ward, Michelle J. Connolly, November 2012, © 2012, Wiley-Blackwell, Hoboken, N.J.).

Femoral Artery

The femoral artery is the main artery that provides oxygenated blood to the tissues of the leg. It passes through the deep tissues of the femoral (or thigh) region of the leg parallel to the femur.

The common femoral artery is the largest artery found in the femoral (thigh) region of the body. It begins as a continuation of the external iliac artery at the inguinal ligament which serves as the dividing line between the pelvis and the leg. From the inguinal ligament, the femoral artery follows the medial side of the head and neck of the femur inferiorly and laterally before splitting into the deep femoral artery and the superficial femoral artery.

The superficial femoral artery flexes to follow the femur inferiorly and medially. At its distal end, it flexes again and descends posterior to the femur before forming the popliteal artery of the posterior knee and continuing on into the lower leg and foot. Several smaller arteries branch off from the superficial femoral artery to provide blood to the skin and superficial muscles of the thigh.

The deep femoral artery follows the same path as the superficial branch, but follows a deeper path through the tissues of the thigh, closer to the femur. It branches off into the lateral and medial circumflex arteries and the perforating arteries that wrap around the femur and deliver blood to the femur and deep muscles of the thigh. Unlike the superficial femoral artery, none of the branches of the deep femoral artery continue into the lower leg or foot.

Like most blood vessels, the femoral artery is made of several distinct tissue layers that help it to deliver blood to the tissues of the leg. The innermost layer, known as the endothelium or tunica intima, is made of thin, simple squamous epithelium that holds the blood inside the hollow lumen of the blood vessel and prevents platelets from sticking to the surface and forming blood clots. Surrounding the tunica intima is a thicker middle layer of connective tissues known as the tunica media. The tunica media contains many elastic and collagen fibers that give the femoral artery its strength and elasticity to withstand the force of blood pressure inside the vessel. Visceral muscle in the tunica media may contract or relax to help regulate the amount of blood flow. Finally, the tunica externa is the outermost layer of the femoral artery that contains many collagen fibers to reinforce the artery and anchor it to the surrounding tissues so that it remains stationary.

The femoral artery is classified as an elastic artery, meaning that it contains many elastic fibers that allow it to stretch in response to blood pressure. Every contraction of the heart causes a sudden increase in the blood pressure in the femoral artery, and the artery wall expands to accommodate the blood. This property allows the femoral artery to be used to detect a person's pulse through the skin (See, e.g., The Cardiovascular System at a Glance, 4th Edition, Philip I. Aaronson, Jeremy P. T. Ward, Michelle J. Connolly, November 2012, 2012, Wiley-Blackwell, Hoboken, N.J.).

Use of the Femoral Artery for Endovascular Procedures

Endovascular diagnostic and therapeutic procedures are generally performed through the femoral artery. Some of the reasons for this generalized approach include its location, easy approach for puncture and hemostasis, low rate of complications, technical ease, wide applicability and relative patient. Femoral puncture also allows access to virtually all of the arterial territories and affords favorable ergonomics for the operator in most instances. This is especially true for most endovascular procedures for treatment of brain pathology, as femoral access typically afford access to all intracranial vessels through a single vascular access site.

Brachial Artery

The brachial artery is a major blood vessel located in the upper arm and is the main supplier of blood to the arm and hand. It continues from the axillary artery at the shoulder and travels down the underside of the arm. Along with the medial cubital vein and bicep tendon, it forms the cubital fossa, a triangular pit on the inside of the elbow. Below the cubital fossa, the brachial artery divides into two arteries running down the forearm: the ulnar and the radial; the two main branches of the brachial artery. Other branches of the brachial artery include the inferior ulnar collateral, profunda brachii, and superior ulnar arteries (See, e.g., The Cardiovascular System at a Glance, 4th Edition, Philip I. Aaronson, Jeremy P. T. Ward, Michelle J. Connolly, November 2012, © 2012, Wiley-Blackwell, Hoboken, N.J.).

Use of the Brachial Artery for Endovascular Procedures

Brachial artery access is a critical component of complex endovascular procedures, especially in instances where femoral access is difficult or contraindicated, such as the absence of palpable femoral pulses, severe common femoral occlusive disease, recent femoral intervention or surgery or femoral aneurysms/pseudoaneurysms. It is a straightforward procedure with a high success rate for percutaneous cannulation (Alvarez-Tostado J. A. et al. Journal of Vascular Surgery 2009; 49(2): 378-385). However, there is a general reluctance to puncture the right brachial artery due to the need to navigate through the innominate artery and arch and due to the risk for complications such as direct nerve trauma and ischemic occlusion resulting in long-term disability (AlvarezTostado J. A. et al. Journal of Vascular Surgery 2009; 49(2): 378-385; Cousins T. R. and O'Donnell J. M. AANA Journal 2004; 72(4): 267-271).

Endovascular Intervention

The current standard for therapeutic recanalization and reperfusion in vascular disease and acute stroke is to perform endovascular interventions via a transthmoral approach, meaning, starting a catheter in the femoral artery at the groin, proceeding through the aorta and carotid artery to the affected blood vessel. All existing devices are designed to be used from this starting point and surgeons are most familiar and comfortable with this route.

Mechanical Endovascular Intervention in Coronary Artery Disease (CAD)

Percutaneous Coronary Intervention (PCT)

Percutaneous coronary intervention (PCI) is a nonsurgical method for coronary artery revascularization. PCI methods include balloon angioplasty, coronary stenting, atherectomy (devices that ablate plaque), thrombectomy (devices that remove clots from blood vessels) and embolic protection (devices that capture and remove embolic debris).

Balloon Angioplasty

Balloon angioplasty involves advancing a balloon-tipped catheter to an area of coronary narrowing, inflating the balloon, and then removing the catheter after deflation. Balloon angioplasty can reduce the severity of coronary stenosis, improve coronary flow, and diminish or eliminate objective and subjective manifestations of ischemia (Losordo D. W. et al. Circulation 1992 December 86(6): 1845-58). The mechanism of balloon angioplasty action involves three events: plaque fracture, compression of the plaque, and stretching of the vessel wall. These lead to expansion of the external elastic lumina and axial plaque redistribution along the length of the vessel (Losordo D. W. et al. Circulation 1992 December 86(6):1845-58).

Coronary Stenting

Coronary stents are metallic scaffolds that are deployed within a diseased coronary artery segment to maintain wide luminal patency. They were devised as permanent endoluminal prostheses that could seal dissections, create a predictably large initial lumen, and prevent early recoil and late vascular remodeling (Krajcer Z. and Howell M. II. Tex I kart Inst J. 2000; 27(4): 369-385).

Drug-eluting stents (DESs) elute medication to reduce restenosis (the recurrence of abnormal narrowing of a blood vessel) within the stents. Local release of rapamycin and its derivatives or of paclitaxel from a polymer matrix on the stent during the 30 days after implantation has been shown to reduce inflammation and smooth muscle cell proliferation within the stent, decreasing in-stent late loss of luminal diameter from the usual 1 mm to as little as 0.2 nun (Stone G. W. et al. N Engl J Med. 2007 Mar. 8. 356(10):998-1008). This dramatically lowers the restenosis rate after initial stent implantation or after secondary implantation of a DES for an in-stent restenosis (Stone G. W. et al. N Engl J Med. 2007 Mar. 8. 356(10):998-1008).

Coronary stents are used in about 90% of interventional procedures. Stent assisted coronary intervention has replaced coronary artery bypass graft. (CABG) as the most common revascularization procedure in patients with coronary artery disease (CAD) and is used in patients with multi-vessel disease and complex coronary anatomy (Kalyanasundaram A. et al. Medscape Dec. 16, 2014; article 164682;medicine.medscape.com/article/164682-overview#a3).

Atherectomy

The directional coronary atherectomy (DCA) catheter was first used in human peripheral vessels in 1985 and in coronary arteries in 1986. In this procedure, a low-pressure positioning balloon presses a windowed steel housing against a lesion; any plaque that protrudes into the window is shaved from the lesion by a spinning cup-shaped cutter and trapped in the device's nose cone (Hinohara T. et al. Circulation 1990 March 81(3 Suppl):IV79-91).

Rotational atherectomy uses a high-speed mechanical rotational stainless steel burr with a diamond chip embedded surface. The burr is attached to a hollow flexible drive shaft that permits it to be advanced over a steerable guide wire with a platinum coil tip. The drive shaft is encased within a Teflon® sheath through which a flush solution is pumped to lubricate and cool the drive shaft and burr. A compressed air turbine rotates the drive shaft at 140,000-200,000 rpm during advancement across a lesion (I linohara T. et al. Circulation 1990 March 81(3 Suppl): IV79-91).

Mechanical Thrombectomy

Intracoronary thrombi may be treated with mechanical thrombectomy devices.

These include rheolytic, suction and ultrasonic thrombectomy devices. In rheolytic thrombectomy, high-speed water jets create suction via the Bernoulli-Venturi effect. The jets exit orifices near the catheter tip and spray back into the mouth of the catheter, creating a low-pressure region and intense suction. This suction pulls surrounding blood, thrombus, and saline into the tip opening and propels particles proximally through the catheter lumen and out of the body (Kalyanasundaram A. et al. Medscape Dec. 16, 2014; article 164682; emedicine.medscape.com/article/164682-overview#a3).

The catheters used for suction thrombectomy act via manual aspiration. These catheters are advanced over a wire to the intracoronary thrombus then passed through the thrombus while suction is applied to a hole in the catheter tip. Large intact thrombus fragments can be removed by means of this technique (Kalyanasundaram A. et al. Medscape Dec. 16, 2014; article 164682; cmcdicine.medscaoe.com/article/164682-overviewita3). Ultrasonic thrombectomy involves the use of ultrasonic vibration to induce cavitation that can fragment a thrombus into smaller components (Choi S. W. et al. J. Intery Cardiol. 2006 Feb. 19(1): 87-92).

Embolization Protection

Embolization (the passage of an embolus (blood clot) within the blood stream) can he caused by the manipulation of guidewires, balloons, and stents across complex atherosclerotic carotid artery lesions (Krajcer Z. and Howell M. H. Tex Heart Inst J. 2000; 27(4): 369-385). Several devices have been developed to trap such embolic material and remove it from the circulation.

The PercuSurge Guardwire is a device that consists of a 0.014- or 0.018-inch angioplasty guidewire constructed of a hollow nitinol hypotube. Incorporated into the distal wire segment is an inflatable balloon capable of occluding vessel flow. The proximal end of the wire incorporates a Microseal™ that allows inflation and deflation of the distal occlusion balloon. When the Microseal adapter is detached, the occlusion balloon remains inflated, at which time angioplasty and stenting are performed. An aspiration catheter can be advanced over the wire into the vessel, and manual suction is applied to retrieve particulate debris (Krajccr Z. and Howell M. H. Tex Heart Inst J. 2000; 27(4): 369-385).

The Medicorp device consists of a protection balloon and a dilation balloon that can be used over a 0.014-inch coronary guidewire. Occlusion above the lesion and below the lesion creates a dilation zone without a flow, which is aspirated and cleared of atherosclerotic debris (Krajcer Z. and Howell M. H. Tex Heart Inst J. 2000; 27(4): 369-385).

Endovascular Treatment of Abdominal Aortic Aneurysms (AAA)

Two endoluminal AAA exclusion stent graft systems have received FDA approval: (i) the Ancure™ Endograft System (Guidant/EVT; Menlo Park, Calif); and (ii) the AneuRx™ device (Medtronic AVE; Santa Rosa, Calif) (Krajcer Z. and Howell M. H. Tex Heart Inst J. 2000; 27(4): 369-385). Both are over-the-wire systems that require bilateral femoral artery access.

The Ancure™ stent graft is an unsupported, single piece of woven Dacron® fabric. The graft is bifurcated and has no intra-graft junctions. The main device is delivered through a 24-Fr introducer sheath; a 12-Fr sheath is required to facilitate the deployment of the contralateral iliac limb. The graft is attached via a series of hooks that are located at the proximal aortic end and at both iliac ends. The hooks are seated transmurally (passing through the vessel wall) in the aorta and the iliac arteries, initially by minimal radial force, and then affixed by low-pressure balloon dilation.

Radiopaque markers are located on the body of the graft for correct alignment and positioning (Krajcer Z. and Howell M. H. Tex Heart Inst J. 2000; 27(4): 369-385).

The AneuRx™ device is a modular 2-piece system composed of a main bifurcation segment and a contralateral iliac limb. The graft is made of thin-walled woven polyester that is fully supported by a self-expanding nitinol exoskeleton. Attachment is accomplished by radial force at the attachment sites, which causes a frictional seal. The main bifurcated body is delivered through a 21-Fr sheath, and the contralateral limb requires a 16-Fr sheath. The body of the graft has radiopaque markers that facilitate correct alignment and positioning (Krajcer Z. and Howell M. H. Tex Heart Inst J. 2000; 27(4): 369-385).

Mechanical Endovascular Neurointervention Mechanical Thrombectomy

Mechanical Thrombectomy

Mechanical thrombectomy (excision of a clot from a blood vessel) devices remove occluding thrombi (blood clots) from the target vessel by a catheter. Subgroups include (1) suction thrombectomy devices that remove occlusions from the cerebral vessels by aspiration (Proximal Thrombectomy) and (2) clot removal devices that physically seize cerebral thrombi and drag them out of the cerebral vessels (Distal Thrombectomy) (Gralla J. et al. Stroke 2006; 37: 3019-24; Brekenfeld C. et al. Stroke 2008; 39: 1213-9).

Proximal Endovascular Thrombcctomv

Manual suction thrombectomy is performed by moving forward an aspiration catheter at the proximal surface of the thrombus (Singh P. et al. J Neurosci Rural Pract. 2013 JulScp; 4(3): 298-303). Manual aspiration is then carried out and the aspiration catheter is taken back under continuous negative pressure. The Penumbra System (Penumbra, Almeda, Calif. USA) is a variation of the manual proximal aspiration method which comprises a dedicated reperfusion catheter attached to a pumping system applying constant aspiration. A second retriever device is similar to a stent and is utilized to take out the resistant clot (Singh P. et al. J Neurosci Rural Pract. 2013 July-September; 4(3): 298-303). The time window for neuroradiological intervention is 8 hours after stroke onset in patients not eligible for intravenous thrombolysis or in patients where intravenous thrombolysis was unsuccessful (Singh P. et al. J Neurosci Rural Pract. 2013 July-September; 4(3): 298-303).

The Penumbra System™ has been examined in a number of clinical trials. The Penumbra Pivotal Stroke Trial was a prospective, single-arm, multicenter study that recruited 125 stroke patients (mean NIHSS 18) within 8 hours of symptom onset and was successful in 81.6% of treated vessels (Penumbra Pivotal Stroke Trial Investigators: The Penumbra pivotal stroke trial: Safety and effectiveness of a new generation of mechanical devices for clot removal in intracranial large vessel occlusive disease. Stroke 2009; 40: 2761-8). However, a good clinical outcome at 90 days was attained in only 25% of patients and in 29% of patients with successful recanalization (the process of restoring flow to or reuniting an interrupted channel such as a blood vessel) of the target vessel (Penumbra Pivotal Stroke Trial Investigators: The penumbra pivotal stroke trial: Safety and effectiveness of a new generation of mechanical devices for clot removal in intracranial large vessel occlusive disease. Stroke. 2009; 40: 2761-8). Poor clinical results occurred despite comparatively better recanalization rates as evidenced by a mortality rate of 32.8% and the occurrence of symptomatic intracerebral hemorrhage (ICH) in 11.2% (Penumbra Pivotal Stroke Trial Investigators: The penumbra pivotal stroke trial: Safety and effectiveness of a new generation of mechanical devices for clot removal in intracranial large vessel occlusive disease. Stroke. 2009; 40: 2761-8).

Distal Endovascular Thrombectomy

Distal thrombectomy is a technically difficult procedure (Singh P. et al. J Neurosci Rural Pract. 2013 July-September; 4(3): 298-303). A number of clinical studies have been carried out using the MERCI (Mechanical Embolus Removal in Cerebral Ischemia) Retriever® device (Concentric Medical, Mountain View, USA), which was the earliest distal thrombectomy device approved by the United States Food and Drug Administration (FDA) (Singh P. et al. J Neurosci Rural Pract. 2013 July-September; 4(3): 298-303). In the initial stage of the procedure, the occlusion site must be traversed with a microcatheter so as to deploy the device beyond the thrombus. The MERCI Retriever® device is pulled back into the thrombus and positioned within the clot. Next, the MERCI Retriever® and the trapped clot are withdrawn, initially into the positioning catheter and then out of the patient's body (Singh P. et al. J Neurosci Rural Pract. 2013 July-September; 4(3): 298-303). Proximal balloon occlusion by means of a balloon guide catheter and aspiration during retrieval of the Merci device is done for the majority of cases in order to prevent thromboembolic complications (Nogueira R. G. et al. Am J Neuroradiol. 2009; 30: 64961; Nogueira R. G. et al. Am J Neuroradiol. 2009; 30: 859-7). During in vivo experimental studies, the distal technique was shown to be more efficient as compared to proximal manual aspiration (Gralla J. et al. Stroke 2006; 37: 3019-24). 100431 The MERCI Retriever® clinical trial was a 25-site, uncontrolled, technical efficacy trial (Smith W. S. et al. Stroke 2005; 36: 1432-8). The trial incorporated 151 patients with occlusion of the internal carotid artery or vertebral and basilar arteries, who did not qualify for intra-arterial therapy (IAT) within 8 hours of symptom onset (Smith W. S. et al. Stroke 2005; 36: 1432-8). Successful recanalization was accomplished in 46%, with excellent clinical outcome in 27.7% of patients (Smith W. S. et al. Stroke 2005; 36: 1432-8). Successful recanalization was linked with distinctly better clinical outcomes. Average procedure time was 2.1 hours, with clinically noteworthy procedural complications occurring in 7.1% and a rate of symptomatic intracranial hemorrhage (ICH) occurring in 7.8% of patients (Smith W. S. et al. Stroke 2005; 36: 1432-8). Despite good clinical outcome, limitations of this device include operator learning curve, the need to traverse the occluded artery to deploy the device distal to the occlusion, the duration required to perform multiple passes with device, clot fragmentation and passage of an embolus within the bloodstream (Meyers P. M. et al. Circulation 2011; 123: 25912601).

Self-Expanding Stents

Until recently, intracranial stenting was restricted to off-label use of balloon-mounted stents intended for cardiac circulation (Singh P. et al. J Neurosci Rural Pract. 2013 July-September; 4(3): 298-303). These stents are not ideal for treating intracranial disease due to their rigidity which makes navigation in the convoluted intracranial vessels difficult (Singh P. et al. J Neurosci Rural Pract. 2013 July-September; 4(3): 298-303). Self-expanding intracranial stents permit stenting in acute stroke that is unmanageable with conventional treatment regimens. The clot occluding the vessel is outwardly displaced by the side of the vessel wall and becomes trapped in the interstices of a self-expanding stent (SES). Wingspan™ (Stryker), Neuroform® (Stryker, Kalamazoo, Mich.), and Cordis Enterprise™ (Cordis Neurovascular, Fremont, Calif.) self-expanding stenting systems have improved steering, cause a reduced amount of vasospasm, and cause a reduced amount of side-branch occlusions as compared to balloon-inflated stents Singh P. et al. J Neurosci Rural Pract. 2013 July-September; 4(3): 298-303). Drawbacks of this method include delayed in-stent thrombosis, the use of platelet inhibitors which may cause intracerebral hemorrhage (ICH) and perforator occlusion from relocation of the thrombus after stent placement (Samaniego E. A. et al Front Neurol. 2011; 2: 1-7; Fitzsimmons B. F. et al. Am J Neuroradiol. 2006; 27: 1132-4; Levy E. I. et al. Neurosurgery 2006; 58: 458-63; Zaidat O. O. et al. Stroke 2008; 39: 2392-5).

Retrievable Thrombectomy Stents

Retrievable thrombectomy stents are self-expandable, re-sheathable, and re-constrainable stent-like thrombectomy devices which combine the advantages of intracranial stent deployment with immediate reperfusion and subsequent retrieval with definitive clot removal from the occluded artery (Singh P. et al. J Neurosci Rural Pract. 2013 July-September; 4(3): 298-303). Removal of the device circumvents the drawbacks associated with permanent stent implantation. These include the requirement for double anti-platelet medication, which potentially adds to the risk of hemorrhagic complications and the risk of in-stent thrombosis or stenosis. The application of retrievable thrombectomy stents is analogous to that of intracranial stents. Under general anesthesia, using a transfemoral approach, a guide catheter is positioned in the proximal internal carotid artery. A guide wire is advanced coaxially over a microcatheter within the blocked intracranial vessel and navigated past the thrombus. The microcatheter is then advanced over the wire through the clot, and the guide wire is substituted for the embolectomy device Singh P. et al. J Neurosci Rural Pract. 2013 July-September; 4(3): 298-303). The revascularization device is placed with the middle third of the device residing within the thrombus formation. The radial force of the stent retriever is able to create a channel by squeezing the thrombus and is able to partially restore blood flow to the distal territory in the majority of cases, producing a channel for a temporary bypass (Singh P. et al. J Neurosci Rural Pract. 2013 July-September; 4(3): 298-303). The device is usually left in place for an embedding time of up to 10 minutes, permitting entrapment of the thrombus within the stent struts. To extract the thrombus, the unfolded stent and the microcatheter are slowly dragged into the guide catheter with flow reversal by continuous aspiration with a 50-ml syringe from the guide catheter Singh P. et al. J Neurosci Rural Pract. 2013 July-September; 4(3): 298-303). The designs of these stents differ in terms of radial strength, design of the proximal and distal stent aperture, stent cell design, material and supplementary intraluminal struts (Mordasini P. et al. Am J Neuroradiol 2011; 32: 294-300; Brekenfeld C. et al. Am J Neuroradiol. 201; 2: 1269-73; Mordasini P. et al. Am J Neuroradiol. 2013; 34: 153-8). Despite the potential to diminish procedure time and to improve recanalization rates, drawbacks to using these devices remain. For example, the TREVO 2 study (Thrombectomy Revascularisation of Large Vessel Occlusions in AIS) was an open label, multicenter trial evaluating the efficacy of the Trevo Pro retriever (Stryker Neurovascular, Fremont, USA) with the Merci device in patients with large vessel ischemic stroke (Nogueira R. G. et al. Lancet 2012; 380: 1231-40). Symptomatic ICH occurred in 6.8% in the Trevo group and in 8.9% of the Merci group, with mortality rates of 33% an 24% respectively. The outcome of this trial sustains the supposition that there are unique mechanical mechanisms of action and consequently dissimilar success and efficacy rates depending on the thrombectomy approaches applied (Singh P. et al. J Neurosci Rural Pract. 2013 July-September; 4(3): 298-303).

Although mechanical endovascular neurointerventions using a transfemoral approach are the current standard for the treatment of acute stroke, it is difficult to access the right internal carotid artery and right vertebral artery via these transfemoral techniques when certain aortic arch variation occurs. A similar transfemoral access problem can occur when vertebral arteries arise at an acute angle from the subclavian artery, or in some variations of the left internal carotid or other vessels.

Aortic Arch

Normal Anatomy

The most common aortic arch branching pattern in humans consists of three great vessels originating from the arch of the aorta. The first branch is the innominate artery (brachiocephalic artery), which branches into the right subclavian artery and the right common carotid artery. The second branch in the most common pattern is the left common carotid artery, and the last branch is the left subclavian artery (Layton K. F. Am J Neuroradiol. 2006; 27: 15411542) (FIG. 3).

Variant Anatomy of the Aortic Arch

Hypoplastic Ascending Aorta

Hypoplasia (underdevelopment or incomplete development) of the ascending aorta usually occurs concomitant with hypoplastic left heart syndrome (HLHS). HLHS comprises a wide spectrum of cardiac malformations, including hypoplasia or atresia (abnormal opening or failure of a structure to be tubular) of the aortic and mitral valves and hypoplasia of the left ventricle and ascending aorta. The great vessels are normally related in this congenital anomaly. HLHS has a reported prevalence of 0.2 per 1000 live births and occurs twice as often in boys as in girls. Left untreated, HLHS is lethal (Kau T. et al. Semin Intervent Radiol. 2007; 24(2): 141-152).

Coarctation of the Aorta

Coarctation of the aorta accounts for about 5 to 7% of all congenital heart disease. It is defined as a discrete stenosis in the proximal descending thoracic aorta. Only those with the most severe obstruction (e.g., aortic arch atresia or interruption) or associated cardiac defects invariably present in infancy (Jenkins N. P., Ward C. Q J M. 1999; 92: 365-371). Most other cases are identified because of a murmur or hypertension found on routine examination. Age at presentation is related to the severity rather than the site of obstruction, as a result of cardiac failure or occasionally cerebrovascular accident, aortic dissection, or endocarditis (Jenkins N. P., Ward C. Q J M. 1999; 92: 365-371). Aortic coarctation may be subclassified into isolated coarctation, coarctation with ventricular septal defect, and coarctation with complex intracardiac anomalies (Backer C. L. et al. Ann Thorac Surg. 2000; 69: S308-S318). An exceedingly rare congenital anomaly is coarctation of a right aortic arch (Maxey T. S. et al. J Card Surg. 2006; 21: 261-263).

Interrupted Aortic Arch

Interrupted aortic arch is defined as the loss of luminal continuity between the ascending and descending aorta and is associated with a multitude of lesions ranging from isolated ventricular septal defects to complex ones (Kau T. et al. Semin Intervent Radiol. 2007; 24(2): 141152). An interrupted aortic arch may be subclassified into anatomical types based on the location of the interruption (Maxey T. S. et al. J Card Surg. 2006; 21: 261-263). Although results have improved, repair of this abnormality is associated with a significant mortality and morbidity (Tchervenkov C. I. et al.

Semin Thorac Cardiovasc Surg Pediatr Card Surg Annu. 2005: 92-102). Patent Ductus Arteriosus A ductus arteriosus Botalli permits blood flow between the aorta (distal to the left subclavian artery) and the pulmonary artery. In a full-term infant, the ductus usually closes within the first 2 days of life. Persistent patency beyond that point is generally permanent, being two to three times as common in girls as in boys. Most of the cases occur as isolated defects. Typical concomitant findings are left ventricle hypertrophy and pulmonary artery dilation. Persistent ductus arteriosus may also be associated with coarctation of the aorta, transposition of the great vessels, and ventricular septal defect (Campbell M. Br Heart J. 1968; 30:4-13).

Thyroid Ima Artery

The thyroid ima artery is a collateral vessel feeding the thyroid gland (Wolpert S. M. Radiology 1969; 92: 333-334). This vessel occurs in up to 16.9% of the population (Vasovic L. et al. Ital J Anat Embryol. 2004;109:189-197). It may be a branch of the aortic arch between the brachiocephalic and left subclavian arteries. However, more frequently it is a branch of the brachiocephalic artery. A further variant of origin is from the right common carotid artery. In the remaining cases, it may originate from the internal mammary, subclavian, or inferior thyroid arteries (Kadir S. In: Kadir S, editor. Atlas of Normal and Variant Angiographic Anatomy. Philadelphia: W B Saunders; 1991. Regional anatomy of the thoracic aorta. pp. 19-54). Aberrant Right Subclavian or Brachiocephalic Artery The right subclavian artery is the last branch of the aortic arch in approximately 1% of individuals (Richardson J. V. et al. Ann Thorac Surg. 1981; 31: 426-432). It courses to the right behind the esophagus in approximately 80% of these cases, between the esophagus and trachea in 15%, and anterior to the trachea or mainstem bronchus in 5% (Kadir S. In: Kadir S, editor. Atlas of Normal and Variant Angiographic Anatomy. Philadelphia: W B Saunders; 1991. Regional anatomy of the thoracic aorta. pp. 19-54).

Right Aortic Arch

Right aortic arch is an uncommon anatomical anomaly that occurs in <0.1% of the population (Cina C. S. et al. J Vasc Surg. 2004; 39: 131-139). It results from the persistence of the right fourth branchial arch (Kadir S In Kadir S, editor. Atlas of Normal and Variant Angiographic Anatomy. Philadelphia: W B Saunders; 1991. Regional anatomy of the thoracic aorta. pp. 19-54). The most common type is the right aortic arch with an aberrant left subclavian artery. The vessels originate in the following order: left common carotid, right common carotid, right subclavian, and left subclavian artery. This type is rarely associated with congenital heart disease. However, symptoms may arise from vascular ring formation (Son J. A. et al. J Card Surg. 1999; 14: 98-102). The mirror-image type (left brachiocephalic trunk, right common carotid and subclavian arteries) is almost always associated with congenital heart disease, especially the cyanotic type (McElhinney D. B. et al. Pediatr Cardiol. 2001; 22:285-291).

Ductus Diverticulum

The aortic isthmus in adults has a variable appearance. Its configuration may show a concavity, a straightening or slight convexity, or a discrete focal bulge. The latter finding represents a ductus diverticulum, present in about 9% of individuals. Representing the most distal segment of the embryonic right arch, the ductus diverticulum is a fusiform dilation of the ventromedial portion of the proximal descending thoracic aorta. At times a prominent ductus diverticulum may resemble a traumatic pseudoaneurysm of the aortic isthmus (Goodman P. C. et al. Cardiovasc Intervent Radiol. 1982; 5: 1-4).

Double Aortic Arch

The double aortic arch is a rare anomaly caused by persistence (to varying degrees) of the fetal double aortic arch system (Kadir S. In: Kadir S, editor. Atlas of Normal and Variant Angiographic Anatomy. Philadelphia: W B Saunders; 1991. Regional anatomy of the thoracic aorta. pp. 19-54). The ascending aorta divides into two arches that pass to either side of the esophagus and trachea and reunite to form the descending aorta. Therefore, it is a form of complete vascular ring, resulting in noncardiac morbidity, but rarely associated with intracardiac defects (Alsenaidi K. et al. Pediatrics. 2006; 118: e1336-e1341). The descending aorta is usually on the left side. Most commonly, one arch is dominant, whereas the other may be of small caliber or represented by a fibrous band.

Cervical Aortic Arch

The cervical aortic arch refers to an unusually high location of the aortic arch in the low or midneck region (Kadir S. In: Kadir S, editor. Atlas of Normal and Variant Angiographic Anatomy. Philadelphia: W B Saunders; 1991. Regional anatomy of the thoracic aorta. pp. 19-54). This rare type of aortic arch anomaly is presumed to result from persistence of the third aortic arch and regression of the normal fourth arch. Abnormalities of brachiocephalic arterial branching and arch laterality are common in patients with a cervical aortic arch (McElhinney D. B. et al. Pediatr Cardiol. 2001; 22:285-291). There is no association with congenital heart disease, and the anomaly occurs most frequently in association with a right aortic arch. Most of the patients with this anomaly are asymptomatic, but symptoms of dysphagia and respiratory distress due to the compression by the vascular ring have been reported (Acikel U. et al. Angiology 1997; 48: 659662).

Bovine Aortic Arch

A common brachiocephalic trunk (also known as the innominate artery), in which both common carotid arteries and the right subclavian artery arise from a single trunk off the arch, is the most frequent normal variant of aortic arch branching (Kadir S. In: Kadir S, editor. Atlas of Normal and Variant Angiographic Anatomy. Philadelphia: W B Saunders; 1991. Regional anatomy of the thoracic aorta. pp. 19-54) (FIG. 4). The innominate artery and the left common carotid artery have a common origin. Therefore, only 2 great vessels originate from the aortic arch (Layton K. F. et al. Am J Neuroradiol. 2006; 27: 1541-1542). Overall, this pattern of branching is seen in approximately 13% of patients (Lippert H, Pabst R. Aortic arch. In: Arterial Variations in Man: Classification and Frequency. Munich, Germany: J F BergmannVerlag;1985:3-10). Although the term bovine aortic arch is ascribed to this anomaly, it is not commonly found in cattle (Layton K. F. et al. Am J Neuroradiol. 2006; 27:1541-1542).

Other Variant Branching

Variations in the sequence of branching of the major arch vessels also occur (<0.5%) (Kadir S. In: Kadir S, editor. Atlas of Normal and Variant Angiographic Anatomy. Philadelphia: W B Saunders; 1991. Regional anatomy of the thoracic aorta. pp. 19-54). For example, the left subclavian artery may be the second branch (before the left common carotid), or the internal and external carotid arteries may originate independently from the aortic arch (Nelson M. L., Sparks C. D. Clin Anat. 2001; 14: 62-65).

Variant Origin of Vertebral Arteries

Various unusual vertebral artery origins exist (Yamaki K. et al. Anat Sci Int. 2006; 81: 100-106; Koenigsberg R. A. et al. Catheter Cardiovasc Interv. 2003;59:244-250). For example, the left vertebral artery arises from the aortic arch, with reported prevalences of 2.4 to 5.8% (Lemke A. J. et al. Am J Neuroradiol. 1999; 20: 1318-1321). The most frequent location is between the left common carotid and subclavian arteries (Kadir S. In: Kadir S, editor. Atlas of Normal and Variant Angiographic Anatomy. Philadelphia: W B Saunders; 1991. Regional anatomy of the thoracic aorta. pp. 19-54). Rarely, the proximal left vertebral artery is duplicated in which one part arises from the arch and the other from the left subclavian, or both originate from the aortic arch. Occasionally, the left vertebral artery is the last branch of the aortic arch, which is rarely true for both vertebral arteries (Goray V. B. et al. Am J Neuroradiol. 2005; 26: 93-95).

The existence of aortic and vertebral artery variations inhibits the treatment of diseases that require end ovascular intervention via a transfemoral approach. For example, the acute angle at which the left common carotid artery branches from the aortic arch in the bovine arch configuration makes mechanical endovascular neurointervention difficult, especially when additional tortuosity (i.e., twists) in the aorta and/or the carotid artery are present. Currently, catheters exist that can access the origin of the left common carotid artery when arterial variations exists. However, when a wire is advanced through these catheters in order to achieve distal access to the artery head, these catheters lack adequate support which results in recoil and displacement into the aortic arch of the advancing wire. The lack of adequate support and the resulting recoil and displacement of the advancing wire make effective treatment impossible. Even when catheterization is achieved in these situations, the process of arriving at the correct combination of catheters and wires results in long treatment delays. In cases of acute stroke, long delays in obtaining access to arteries often leads to additional irreversible cell death with additional permanent neurologic injury. Additionally, with aging the anatomy of the takeoff of the great vessels often changes, which can make access to the cerebral vasculature more difficult. This is particularly problematic as with aging the incidence of major thromboembolic strokes, for which emergent endovascular thrombectomy is often the best treatment, also increases The branching pattern of the brachiocephalic branch from the aortic arch was categorized into three types based on the vertical distance from the origin of the brachiocephalic branch to the top of the arch, which determined the arch type. This distance was less than 1 diameter of the left common carotid artery (CCA) for a type-1 aortic arch, between 1 and 2 CCA diameters for a type-2 aortic arch, and nd greater than 2 CCA diameters for a type-3 aortic arch.— http://www.pagepressjournals.org/index.php/gc/article/view/5720/5861—"We explored the relationship between aging and the configuration of the aortic arch using computed tomography angiography (CTA). "We retrospectively reviewed CTA obtained in 140 cases. The configuration of the aortic arch was categorized into three types based on the criteria mentioned by Madhwal et al., and the relationships between each configuration and patient characteristics were analyzed. Anomalies of the aortic arch were also explored. Twenty patients had a type-1 aortic arch (mean age, 56.1 years), 30 patients had a type-2 aortic arch (mean age, 66.3 years), and 89 patients had a type-3 aortic arch (mean age, 71.7 years). The mean age of patients with a type-3 aortic arch was significantly higher than that of patients with a type-1 aortic arch. No significant correlations between the type of aortic arch and other factors, such as smoking habit, were seen. The configuration of the aortic arch in our study appears to be significantly affected by the age of the patients." "Among 140 patients, 139 patients exhibited the left aortic arch. One patient showed the right aortic arch. Of the 139 patients with the left aortic arch, 20 patients had a type-1 aortic arch (14.4%; mean age, 56.1±18.0 years), 30 patients had a type-2 aortic arch (21.6%; mean age, 66.3±11.5 years), and 89 patients had a type-3 aortic arch (64.0%; mean age, 71.7±9.8 years). The mean age of the patients with a type-3 aortic arch was significantly higher than that of the patients with a type-1 aortic arch. The mean age of the patients with a type-2 aortic arch was higher than that of the patients with a type-1 aortic arch, although the difference was not significant. No significant correlations between the branching type and other patient characteristics, such as sex, smoking habit, hypertension, and diabetes mellitus, were observed (Table 1). "Regarding the anatomical variations among the aortic arches, 118 patients (84.3%) had a normal-type aortic arch with three branches (the brachiocephalic trunk, the left CCA, and the left subclavian artery). The bovine aortic arch was present in 20 cases (14.2%). Ten patients showed both a type-3 aortic arch and a bovine aortic arch (7.2%). For some of the patients showing these two characteristics, the navigation of the guiding catheter into the left CCA was difficult." The vessel twists and turns and resulting recoil and displacement have in part been addressed by using a "Simmons" also known as the Sidewinder/shepherd's hook catheter. However, the Simmons has two significant short comings: first these catheters only maintain their shape when they are unconstrained and second, passing a wire through a Simmons it will result changing the shape of the Simmons and alter the direction of the hole at the end of the Simmons. The present invention surmounts theses short comings by specifically changing the structural configuration of the present invention (by changing number of segments, segment length, number of bends and amount of bend angle) of the elements of the present invention to rest upon, bracing, abutting and otherwise using anatomical structures proximal to various elements of the present invention to ameliorate or prevent the difficulties associated with "Simmons" also known as the Sidewinder/shepherd's hook catheter.

Therefore, a need exists for an endovascular device capable of treating diseases that require endovascular intervention in a patient suffering from a blood vessel anomaly or variant. The described invention provides an endovascular device capable of effectively treating such patients by providing support and thus preventing recoil and displacement of an advancing wire, catheter, or other device, resulting in distal blood vessel access, clot retrieval, embolization of an aneurysm and/or embolization of an arteriovenous malformation (AVM), or other desired medical procedure.

SUMMARY OF THE INVENTION

According to one aspect, the described invention provides an endovascular device comprising: a tube comprising: a first segment of at least 20 cm in length and an internal diameter of from 0.01 French to 30 French wherein said first segment has a first end which is an external termination device such as a leur lock or diaphragm and a second end terminating in a first bend, wherein said first bend is 90 degrees plus or minus 35 degrees and connected to a second segment of said tube; said second segment of at least 3 cm in length and no more than 35 cm in length and an internal diameter of from 0.01 French to 30 French wherein said second segment has a first end which terminates in said first bend and a second end which terminates in said second bend, wherein said second bend is 90 degrees plus or minus 60 degrees and connected to a third segment of said tube; and said third segment of at least 0.5 cm in length and an internal diameter of from 0.1 French to 30 French wherein said third segment has a first end which terminated in said second bend and connected to said second segment of said tube and a second end which terminated in said third bend, said third segment of at least 3 cm in length and no more than 35 cm in length and an internal diameter of from 0.01 French to 30 French wherein said third segment has a first end which terminated in said second bend and a second end which terminates in said third bend, wherein said third bend is 90 degrees plus or minus 60 degrees and connected to a fourth segment of said tube; and said fourth segment of at least 0.5 cm in length and an internal diameter of from 0.1 French to 30 French wherein said fourth segment has a first end which terminated in said third bend and connected to said third segment of said tube and a third end which is a hole. Said tube may have more than one lumen, as well as one or more valves or no valves at all. The present invention is compatible for use with multi-lumen catheters. Specifically, the present invention's tube may incorporate or contain one or more multi-lumen catheters.

In the preferred embodiment said second segment is semi-ridged. In particular, in the preferred embodiment said second segment should have the stiffness of between that of rubber 0.0006 GPa and polyethylene 0.117 GPa at room temperature. Please note that gigapascals (GPa) is a measure of shear in thousands of pounds per square inch (ksi). It should be further noted that a segment system is composed of at least one segment plus either an end hole or a bend.

The present invention minimizes the use of wire which may cause unintended perforations by using the geometry of the catheter of the present invention to position the catheter. Said geometry allows the user to place the disclosed catheter of the present invention proximally to an appropriately targeted arch fulcrum, and rotate the present invention into position without the use of wires. However, wires may optionally be used. The particular advantage of the present invention rests in having the catheter oriented so that the second segment of the catheter of the current invention rests on the lesser/inferior curve of the aortic arch, and is supported by said lesser curve. This will resist recoil of said catheter when additional devices which can include wires, additional catheters, and/or other devices are advanced more distally through the distal end hole of the current invention to a desired target location. In order to achieve said advantages the following method should be employed: the present invention should be attached at the distal end of a delivery system; then said delivery system positioned within a body lumen at a target arch or other vessel structure capable of providing support against kick back of the present invention; the delivery system should be removed leaving the present invention proximal to said target arch or other vessel structure capable of providing support against kick back of the present invention, then positioning segment one of the present invention such that the proximal end of said segment one extends down a vessel below the fulcrum formed by the top of the lesser/inferior curve of said target arch and terminates at an external termination device outside the body, while said segment two's center rests on the fulcrum formed by the top of said lesser/inferior curve of said target arch (or alternatively on top of any other vessel structure which structure capable of providing support against kick back of the present invention—such as at the junction of two relatively perpendicular vessels); then positioning segment two of the present invention such that said segment two's center rests on the fulcrum formed by the top of the lesser/inferior curve of said target arch while the segment three of the present invention rests along a vessel wall opposite the next vessel curve (or alternatively abutting or bracing any other vessel structure which structure capable of providing support against kick back of the present invention—such as at the side wall near the junction of two relatively perpendicular vessels), then positioning segment three and four of the present invention such that the distal end-hole of said segment four extends into the target vessel; and finally advancing additional wires, catheters, or other devices through the tube formed by the combination of all the segment of the present invention into the distal vasculature of said target vessel to complete the desired medical procedure. It should be noted that the present invention has at least four segments and at least three bends, thus the method of use must be amended so that at least two segments and preferably more segment are on positioned (on top of, abutting, bracing) various vessel structures perpendicular to kick back forces generated by pushing wires through the tube formed by the segments and bends of the present invention.

These and other advantages of the invention will be apparent to those of ordinary skill in the art by reference to the following detailed description and the accompanying drawings.

DETAILED DESCRIPTION OF THE INVENTION

The term "recoil and displacement", as used herein refers to the phenomenon of catheter prolapse or displacement (slipping forward, back, or down, and out of the desired position) due to a counterforce against the catheter by the advancing wire, second catheter, or other additional device.

Figure 1:
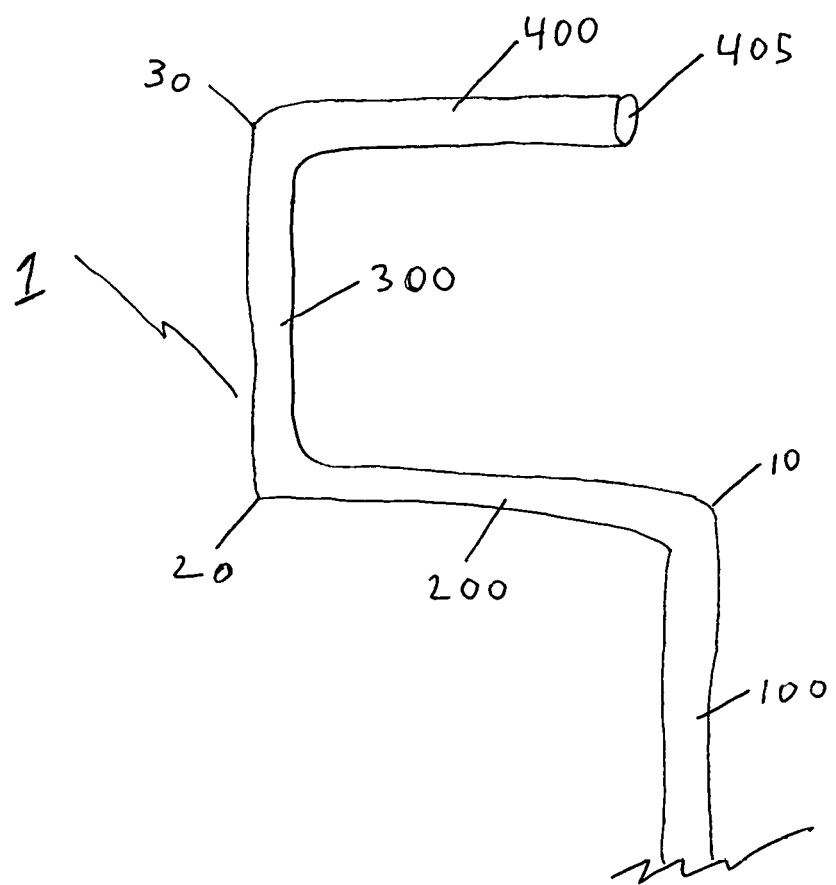
FIG. 1 shows an illustration of a side view of the described invention.

Now referring to FIG. 1, the present invention has seven principal elements. The first three of said elements are bends (10, 20 and 30), and four are segments (100, 200, 300 and 400) of the tube 1. More particularly, the first bend 10 connects segment one 100 to segment two 200 at an angle of 90 degrees plus or minus 35 degrees. Segment one 100 has a length of at least 20 cm in length and an internal diameter of from 0.01 French to 30 French. Segment one has both first and second ends.

Segment two 200 measures at least 3 cm in length and no more than 35 cm in length. Segment two 200 has an internal diameter of from 0.01 French to 30 French. Segment two 200 has a first end which terminated in first bend 10 and a second end which terminates in second bend 20. Second bend 20 has an angle of 90 degrees plus or minus 60 degrees.

Second bend 20 connects to segment three 300 of tube 1. Segment three 300 measures at least 0.5 cm in length and has an internal diameter of from 0.01 French to 30 French.

Segment three 300 has a first end which terminates in second bend 20 and a second end which terminates in second bend 20.

Segment three 300 measures at least 3 cm in length and no more than 35 cm in length. Segment three 300 has an internal diameter of from 0.01 French to 30 French. Segment three 300 has a first end which terminated in second bend 20 and a second end which terminates in third bend 30. Third bend 30 has an angle of 90 degrees plus or minus 60 degrees.

Third bend 30 connects to segment four 400 of tube 1. Segment four 400 measures at least 0.5 cm in length and has an internal diameter of from 0.01 French to 30 French. Segment four 400 has a first end which terminates in third bend 30 and connected to segment three 300 of tube 1, and a second end terminating at distal hole 405.

Figure 2:
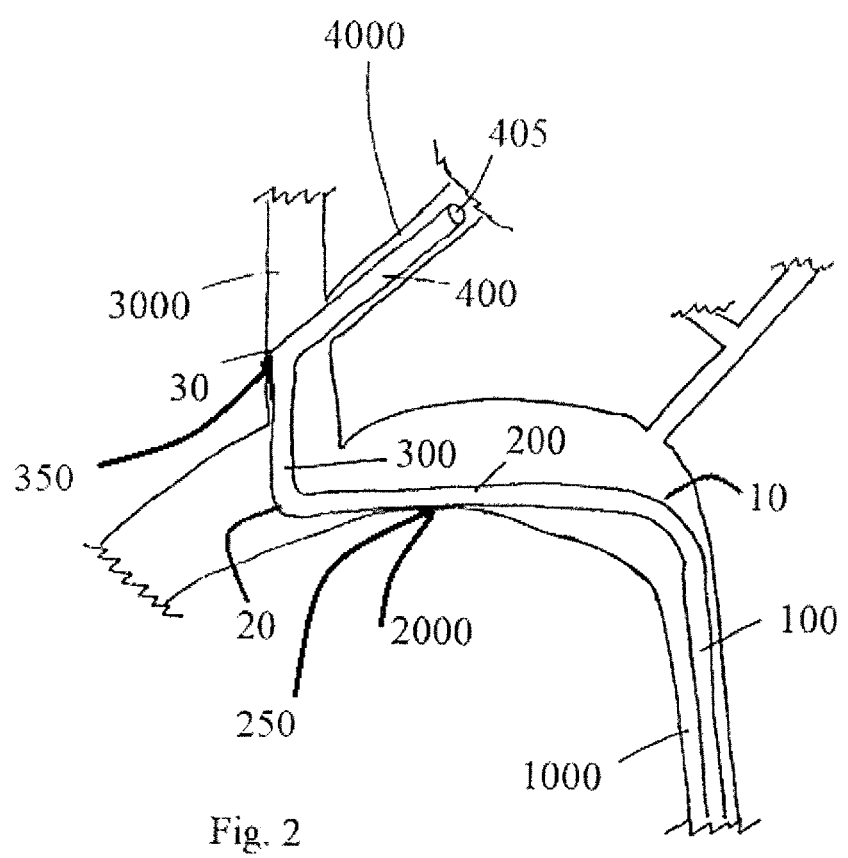
FIG. 2 shows an illustration of a cross-sectional view of one embodiment of the described invention in place with the second segment resting on the arch fulcrum, with the third segment bracing a vessel and with the fourth segment inserted into a side vessel.

Now referring to FIG. 2, the present invention is shown deployed in the aorta. Segment one 100 is deployed downwardly in the ascending aorta 1000, which is located below the fulcrum formed by the arch of the aorta 2000. The middle of segment two 200 is shown resting on the fulcrum formed by the arch of the aorta 2000. Segment three 300 is shown in this example being upwardly deployed into the Innominate artery 3000. Segment four 400 is shown in this example being upwardly deployed into a side vessel 4000.

According to one embodiment, the segment two 200 has ridges to promote stability at the focal point 2000. According to another embodiment, the segment two 200 is coated with an elastic material to deform atop the fulcrum point 2000 for improved securement. Similarly, according to another embodiment, the segment three 300 has ridges to promote stability at the wall of Innominate artery 3000. According to another embodiment, the segment three 300 is coated with an elastic material to deform atop the Innominate artery 3000 for improved securement. According to yet another embodiment both segments two 200 and segment three 300 have ridges and elastic material coating to promote stability.

The various components of the described invention may be comprised of one or more materials. Thermoplastics include, but are not limited to, nylon, polyethylene terephthalate (PET), urethane, polyethylene, polyvinyl chloride (PVC) and polyether ether ketone (PEEK).

Thermosets include, but are not limited to, silicone, polytetrafluoroethylene (PTFE) and polyimide.

Composites include, but are not limited to, liquid crystal polymers (LCP). LCPs are partially crystalline aromatic polyesters based on p-hydroxybenzoic acid and related monomers. LCPs are highly ordered structures when in the liquid phase, but the degree of order is less than that of a regular solid crystal. LCPs can be substituted for such materials as ceramics, metals, composites and other plastics due to their strength at extreme temperatures and resistance to chemicals, weathering, radiation and heat. Non-limiting examples of LCPs include wholly or partially aromatic polyesters or copolyesters such as XYDAR® (Amoco) or VECTRA® (Hoechst Celanese). Other commercial liquid crystal polymers include SUMIKOSUPER™ and EKONOL™ (Sumitomo Chemical), DuPont™ and DuPont ZENITE™ (E.I. DuPont de Nemours), RODRUN™ (Unitika) and GRANLAR™ (Grandmont).

According to some embodiments, the angled extension comprises a shape memory polymer (SMP). Shape memory polymers include, but are not limited to methacrylates, polyurethanes, blends of polystyrene and polyurethane, and polyvinylchloride. According to some embodiments, the angled extension of the catheter comprises a shape memory alloy (SMA). Non-limiting examples of shape memory alloys include nickel-titanium (i.e., nitinol).

According to some embodiments, the described invention can be used in an endovascular procedure in a subject suffering from an anatomical variation in a blood vessel. According to some embodiments, the blood vessel comprises an anatomical variation comprising tortuosity. According to some embodiments, the blood vessel comprises an anatomical variation comprising an acute angulation. According to some embodiments, the acute angulation is an aortic arch variation. According to some embodiments, the aortic arch variation is a bovine arch variation. According to some embodiments the anatomic variation is a Type II aortic arch. According to some embodiments the anatomic variation is a Type III aortic arch. According to some embodiments, the acute angulation is a vertebral artery variation. It should be noted that the present invention is configured to facilitate the deployment of the present invention. Said configuration may be implemented prior to the insertion of the present invention in to the patient's vessels or may be configured after the insertion of the present invention in to the patient's vessels. Said configuration includes lengthening or shortening the segments and changing the angles of the bends. The lengthening or shortening the segments may be achieved mechanically by cutting segment and bend the bends outside the patient's vessels. The lengthening or shortening the segments may be achieved inside the patient's vessels by exposing the segments to radiation. Also once the present invention is inserted into a patent's vessels, the shaping of the bends may be achieved either mechanically by twisting the present invention, by moving wires inside the present invention or by exposing the segments to radiation.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials have been described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise.

The publications discussed herein are provided solely for their disclosure prior to the filing date of the present application and each is incorporated by reference in its entirety. Nothing herein is to be construed as an admission that the present invention is not entitled to antedate such publication by virtue of prior invention. Further, the dates of publication provided may be different from the actual publication dates which may need to be independently confirmed.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A method of using an endovascular medical device comprising:
    (a) providing an endovascular medical device having a single tube positionable within a vasculature of a patient, said single tube comprising:
        (i) a first segment of at least 20 cm in length and an internal diameter of from 0.01 Fr to 30 Fr, said first segment including:
            a first end comprising an external termination device; and
            a second end terminating in a first bend,
            wherein said first bend is 90 degrees plus or minus 35 degrees;
        (ii) a second segment connected to said first segment, said second segment configured to rest on the vascular arch to prevent recoil, said second segment having a length of at least 3 cm and no more than 35 cm and an internal diameter of from 0.01 Fr to 30 Fr, said second segment including:
            a first end terminating in said first bend; and
            a second end terminating in a second bend,
            wherein said second bend is 90 degrees plus or minus 60 degrees;
        (iii) a third segment connected to said second segment, said third segment having a length of at least 0.5 cm and an internal diameter of from 0.01 Fr to 30 Fr, said third segment including:
            a first end terminating in said second bend and a second end terminating in a third bend,
            wherein said third bend is 90 degrees plus or minus 60 degrees; and
        (iv) a fourth segment connected to said third segment, said fourth segment having a length of at least 0.5 cm and an internal diameter of from 0.01 Fr to 30 Fr, said fourth segment including:
            a first end terminating in said third bend and a second end terminating in a hole;
    (b) attaching said device to a distal end of a delivery system;
    (c) positioning said delivery system in proximity to said vascular arch:
    (d) disconnecting said delivery system from said device,
    (e) positioning said device such that the first segment is positioned proximally of a top of a lesser/inferior curve of said vascular arch and terminates at the external termination device outside the patient such that the lesser/inferior curve of said vascular arch acts as said fulcrum to prevent prolapse or displacement;
    (f) positioning said second segment of said device such that said second segment rests on said fulcrum;
    (g) positioning said third segment such that said third segment rests along a vascular wall opposite a curve located distally of said vascular arch;
    (h) positioning said device such that said hole at said second end of said fourth segment extends into a target vessel located distally of said vascular arch; and
    (i) advancing additional wires, catheters, or other devices through said single tube of the device into distal vasculature of said target vessel to perform a desired medical procedure.

2. The method of claim 1, wherein said external termination device comprises a Luer Lock.

3. The method of claim 1, wherein said external termination device comprises a diaphragm.

4. The method of claim 1, wherein at least one of the segments includes an elastic coating to promote stability.

5. The method of claim 1, wherein said second segment comprises a stiffness of between 0.0006 gigapascals (GPa) and 0.117 GPa.

6. The method of claim 1, wherein the single tube assumes desired first, second and third bends when placed within a vasculature and prior to insertion of an additional device through a lumen of the single tube, the bends of the single tube used to position the tube.

7. A method of performing an endovascular medical procedure comprising:
    positioning a tubular member defining a single lumen extending therethrough such that a first segment of the tubular member is located within a patient's ascending aorta;
    positioning a second segment of the tubular member in abutment with an inferior curve of the patient's aortic arch;
    positioning a third segment of the tubular member in abutment with an interior wall of a vessel distal of the aortic arch such that the aortic arch acts as a fulcrum for the tubular member to resist prolapse and displacement during advancement of a supplemental medical device through the tubular member; and
    positioning a fourth segment of the tubular member within a target vessel distal of the aorta;
    advancing the supplemental medical device through the tubular member and into the target vessel, wherein advancing the supplemental medical device includes:
        passing the supplemental medical device through a first bend positioned between the first segment and the second segment;
        passing the supplemental medical device through a second bend positioned between the second segment and the third segment; and
        passing the supplemental medical device through a third bend positioned between the third segment and the fourth segment, during which, the tubular member resists recoil forces applied by the supplemental medical device via abutment of the tubular member with an inferior curve of the aortic arch and the interior wall of a vessel branching off the aortic arch.

8. The method of claim 7, wherein passing the supplemental medical device through the first bend, the second bend, and the third bend includes deflecting the medical device more than 90 degrees.

9. The method of claim 7, further comprising performing the endovascular procedure using the supplemental medical device.

* * * * *